United States Patent [19]

Blay et al.

[11] 4,352,738

[45] Oct. 5, 1982

[54] ANAEROBIC FILTER

[75] Inventors: George A. Blay; Enrique R. Witt, both of Corpus Christi, Tex.

[73] Assignee: Celanese Corporation, New York, N.Y.

[21] Appl. No.: 205,388

[22] Filed: Nov. 10, 1980

Related U.S. Application Data

[63] Continuation-in-part of Ser. No. 95,915, Nov. 19, 1979, abandoned.

[51] Int. Cl.$^3$ .............................................. C02F 3/28
[52] U.S. Cl. .................................... 210/612; 210/614; 210/617
[58] Field of Search ............... 210/601, 603, 605, 612, 210/613, 614, 616–618, 630

[56] References Cited

U.S. PATENT DOCUMENTS

| | | | |
|---|---|---|---|
| 4,134,830 | 1/1979 | Skogman et al. | 210/16 |
| 4,145,279 | 3/1979 | Selby | 210/17 |
| 4,182,675 | 1/1980 | Jeris | 210/20 |

FOREIGN PATENT DOCUMENTS 2520742  11/1975  Fed. Rep. of Germany ...... 210/603

OTHER PUBLICATIONS

Lovan et al. "The Anaerobic Filter for the Treatment of Brewery Press Liquor Waste," Brewers Digest, Feb. 1972, pp. 66–73.
Bellegem et al. "The Anaerobic Treatment of Waste Water of the Potato Starch Industry," Dec. 1974 issue of TNO project, pp. 1–21.
Jennett et al., "Anaerobic Filter Treatment of Pharmaceutical Waste," JWPCF, Jan. 1975, pp. 104–121.
Young et al. "The Anaerobic Filter for Waste Treatment," JWPCF, May 1969, pp. R160–173.
De Walle et al. "Kinetics of Substrate Removal in a Completely Mixed Anaerobic Filter," Biotech. & Bioeng., 1976, pp. 1275–1295.
Chan et al., "Treatment of High Strength Acidic Wastewater with a Completely Mixed Anaerobic Filter," Water Research, 1977, pp. 295–304.
El-Shafie et al. "Anaerobic Treatment in a Multiple Upflow Filter System," JWPCF, Nov. 1973, pp. 2345–2357.
Donovan et al. "Treatment of High Strength Wastes with an Anaerobic Filter," Presented AICHE 86th Nat. Meeting, Apr. 1979, pp. 1–30.
Graef et al. "Stability and Control of Anaerobic Digestion," JWPCF, Apr. 1974, pp. 666–683.
Lawrence et al. "The Role of Sulfide in Preventing Heavy Metal Toxicity in Anaerobic Treatment," JWPCF, Mar. 1965, pp. 392–405.
Clark et al., "The pH Tolerance of Anaerobic Digestion," Presented at 5th Inter. Water Pollution Research Conf., Aug. 1970, pp. II-27/1–14.
Lettinga "Direct Anaerobic Treatment Handles Wastes Efficiently" Industrial Wastes, Jan./Feb. 1979, pp. 18–24,40,41.

Primary Examiner—Peter A. Hruskoci
Attorney, Agent, or Firm—Abner Sheffer

[57] ABSTRACT

In the operation of a recycling anaerobic filter for treating aqueous waste streams, the rate of production of methane is measured continually at frequent intervals and the COD feed rate is varied to maintain a predetermined, timed, relationship between that varied feed rate and the measured methane production rate.

9 Claims, 10 Drawing Figures

ANAEROBIC FILTER

This is a continuation-in-part of U.S. application Ser. No. 095,915 filed Nov. 19, 1979, now abandoned whose entire disclosure is incorporated herein by reference.

This invention relates to the operation of a recycling methane-producing anaerobic filter, of the type described in Witt et al German published application p274831.32, published April 1978, and corresponding U.S. application Ser. No. 57,545 filed July 13, 1979, whose entire disclosure is incorporated herein by reference.

As is known in the art, a methane-producing anaerobic filter contains two types of bacteria living in symbiotic relationship. The "acid formers" degrade large molecules to 1-3 carbon molecules (acetic acid, propionic acid, etc.), mostly acidic; they are more resistant to variations of pH, temperature, and food concentrations. The "methane formers" consume the acids and small molecules by dismutation; one carbon is completely oxidized to $CO_2$ and a second carbon is reduced to methane. Carbon dioxide is partially soluble in water, and some $CO_2$ remains combined with the alkalinity present; the rest escapes into the gas phase. Methane is essentially insoluble and is completely expelled into the gas phase. In the literature it is noted that the relative amounts of carbon dioxide and methane in the evolved gas may vary during the process. For instance Jennett and Dennis in "Anaerobic filter treatment of pharmaceutical waste", Journal WPCF 47, 104–121 (1975) show (FIGS. 9 and 10) methane contents of some 60 to 85%; Young and McCarty in "The Anaerobic Filter for Waste Treatment", Journal WPCF 41, R160–173 (1969) show methane contents of about 70 to 80%. The methane content of the gas is related to the nature of the feed; thus the theoretical $CH_4:CO_2$ ratio in the process products is 1:3 for formic acid, 1:1 for acetic acid and 3:1 for methanol.

The operations of anaerobic filters are often discussed in terms of the "organic load" (hereafter "OL") on the filter, i.e. the rate of feed of COD (chemical oxygen demand) per unit volume of the filter. This may be expressed as "lbs COD/cu ft/day"; those units are used herein unless otherwise noted. OL may also be expressed as "kg COD/cu m/day"; 0.5 lb COD/cu ft/day equals 8 kg COD/cu m/day.

As disclosed in the above-mentioned Witt et al application, the recycling anaerobic filter is operated at a loading (OL) that is generally above 0.2 (and preferably at least about 0.5) lb COD/cu ft/day.

The accompanying drawings illustrate some aspects of this invention.

FIG. 1 is a schematic view of an anaerobic filter and of control devices therefor.

FIGS. 2, 3 and 4 are graphs showing OL and KL values and pH values (obtained once a day) during several sequences of operation. FIGS. 2 and 3 relate to Example 1 (FIG. 3 is a continuation of FIG. 2). FIG. 4 relates to Example 4.

Figure 7:
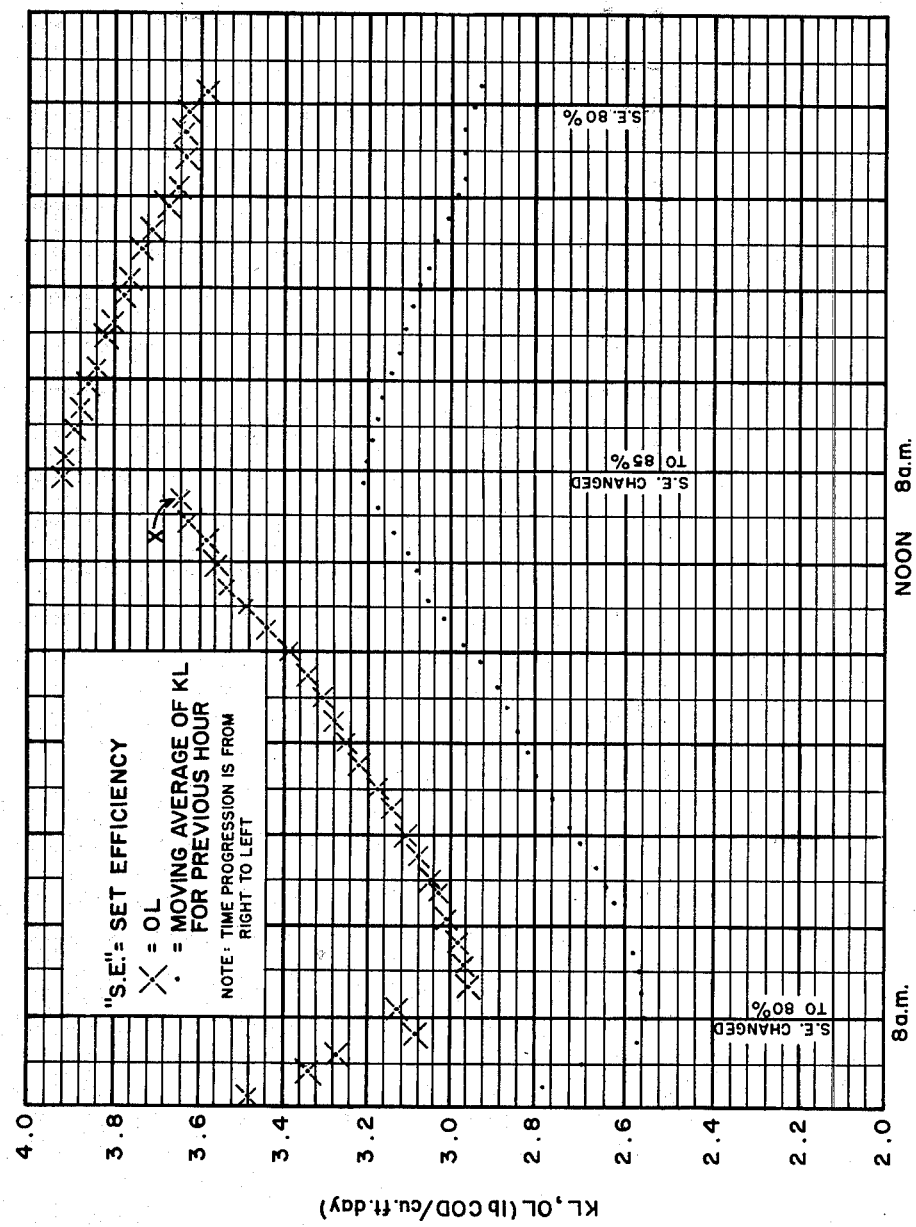
Figure 7A:
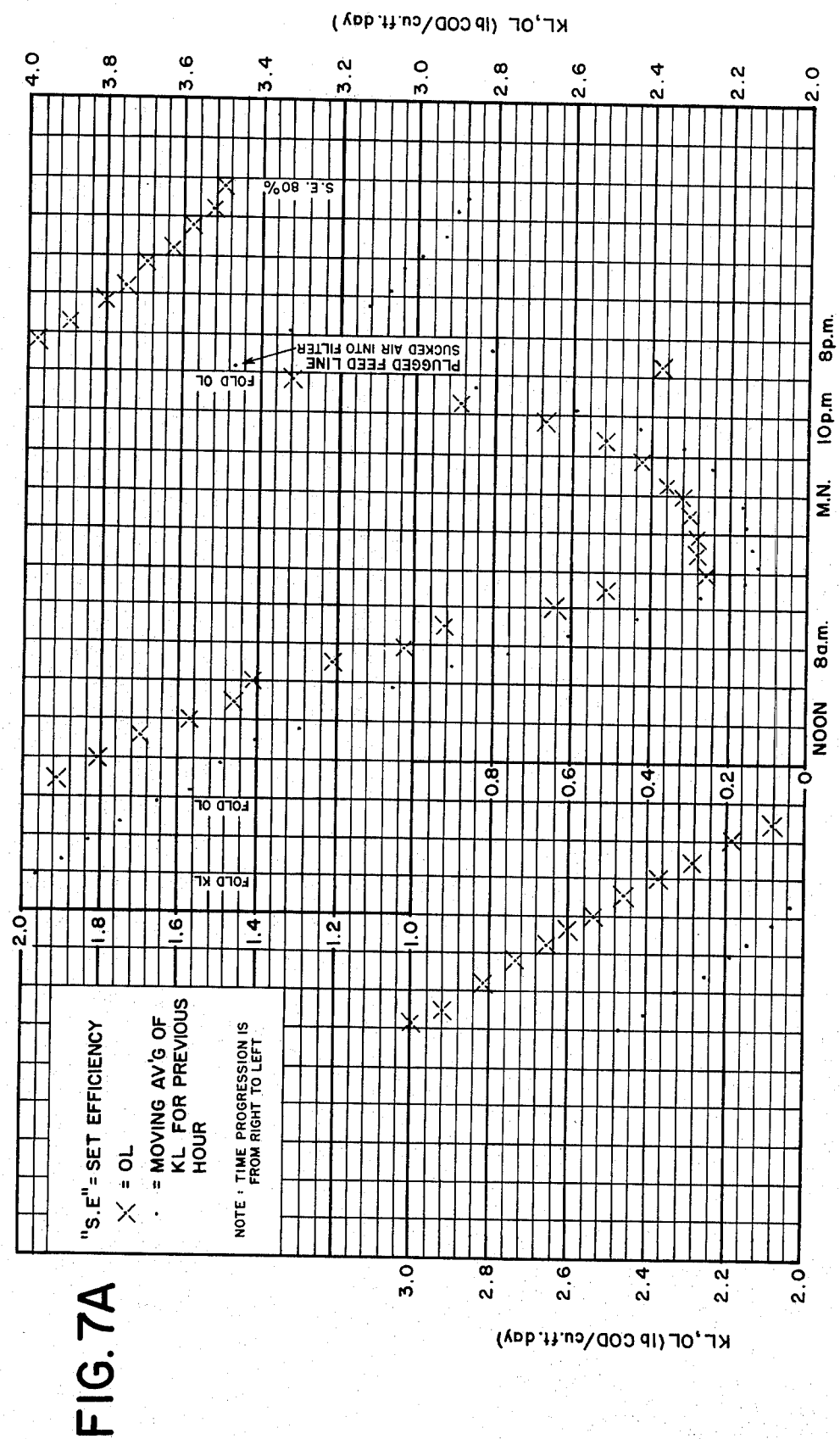
Figure 8:
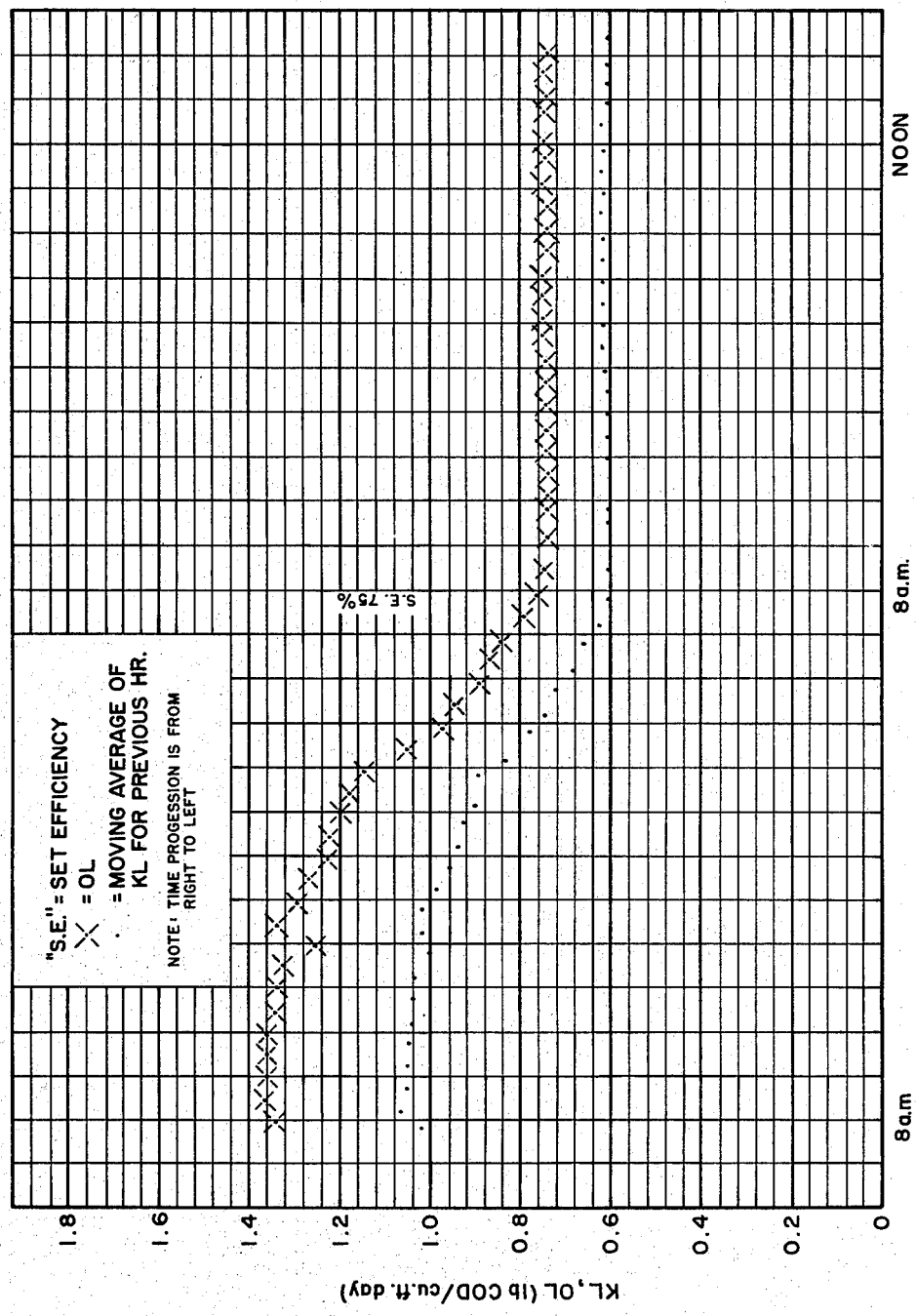
Figure 9:
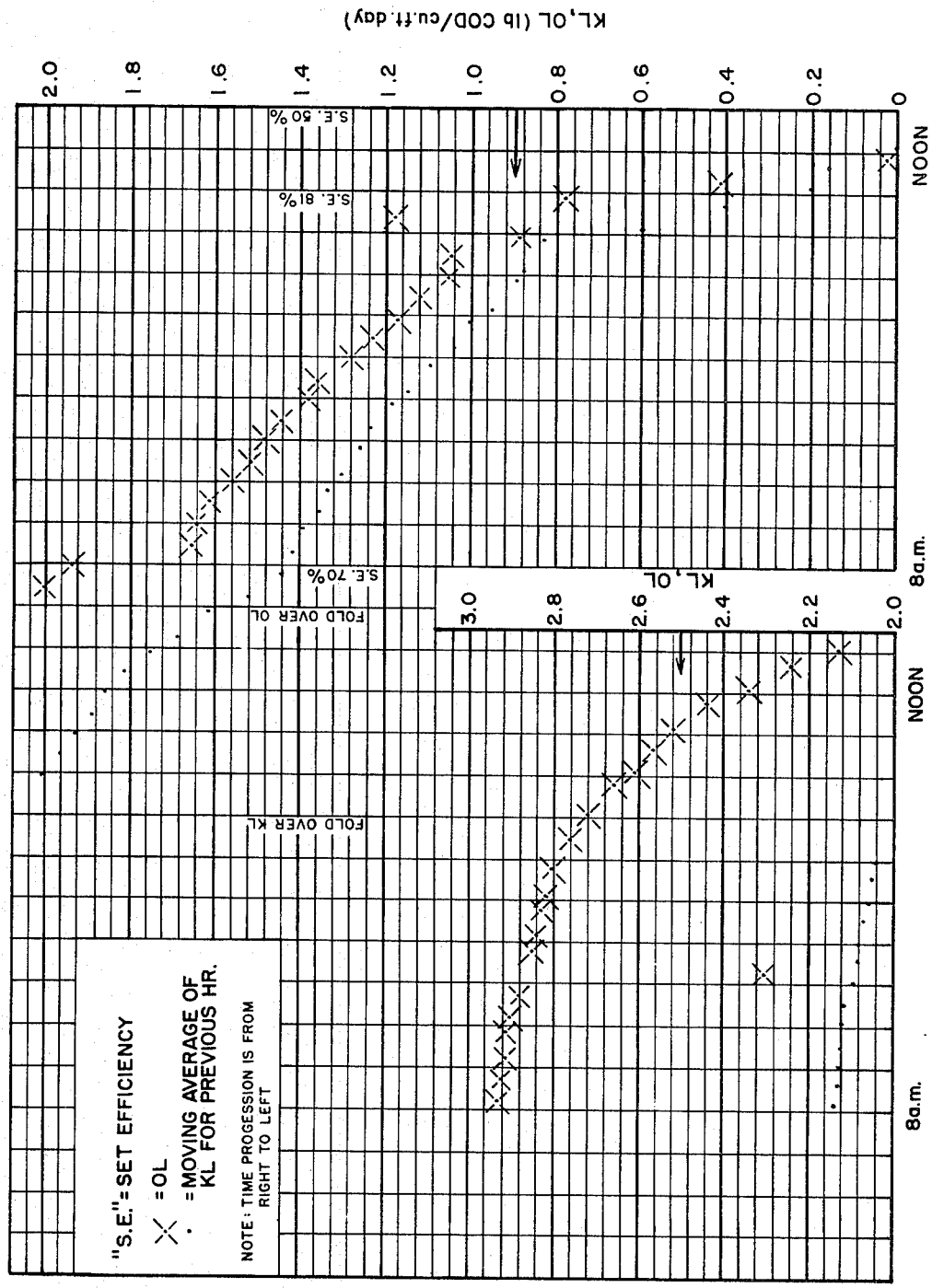

FIGS. 7, 7A, 8 and 9 are charts of OL and KL values recorded automatically at staggered one hour intervals. FIGS. 7 and 7A cover a period of about 3½ days toward the end of Example 4 (FIG. 7A is a continuation of FIG. 7). FIGS. 8 and 9 are for two-day periods during Examples 2 and 5, respectively.

FIGS. 7 to 9 show instantaneous values of OL, taken at hourly intervals, and moving average values of KL (for the preceding hour) also taken at hourly intervals 20 minutes behind OL values. For example, an instantaneous OL value is recorded at 8:00; at 8:20 the moving average KL value (averaged over the period from 7:20 to 8:20) is recorded; at 9:00 a new instantaneous OL is recorded, at 9:20 the moving average KL value (averaged over 8:20 to 9:20) is recorded, and so on. In FIGS. 7A and 9 the legends "fold over" will be noted. This indicates of course that the values have gone past the upper limit of the scale of the chart and that the next values are to be read on a new scale, also shown. (There are two recorded points, located between 8 and 10 PM on the first day of FIG. 7A, which applicants do not understand in that it is not clear just which scale applies to those points.)

Figure 5:
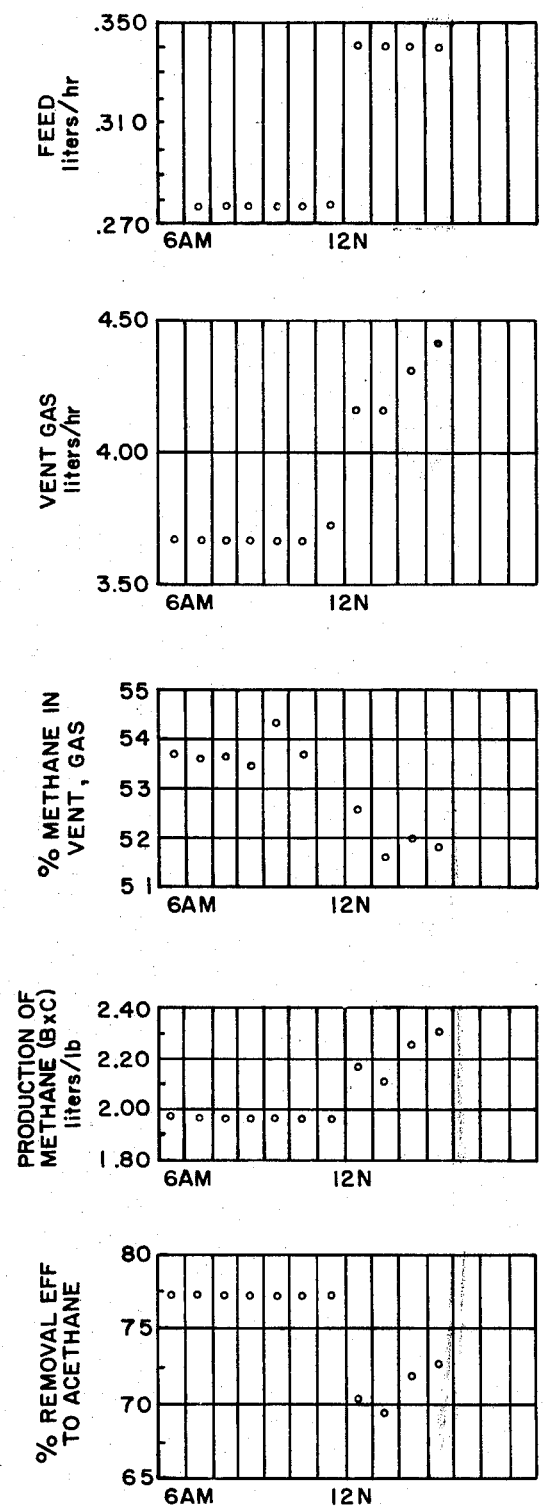
FIG. 5 is a collection of graphs showing the changes in vent gas, % methane in vent gas, production of methane and methane efficiency over a period of several hours in response to a change in feed rate.

We have discovered that in an operating recycling methane-producing anaerobic filter the rate of production of methane is delicately and quickly responsive to even small changes in conditions. FIG. 5 illustrates some features of the response, obtained with a recycling anaerobic filter having a void volume of 20 liters, operated at a recycle rate of 12 liters per hour. The feed rate to this filter at the beginning was about 0.28 l/hr of a feed containing about 25 g COD/l; this corresponds to an OL of about 0.52 lb COD/cu ft/day, and a detention time of about 71.5 hours. At the beginning, the methane efficiency was about 76% and the COD concentration in the blend (of fresh feed and recycle stream) being fed to the base of the filter was about 6.4 g COD/l. The feed rate was then changed sharply to raise the OL to about 0.62, this caused the COD concentration in the blend being fed to the filter to change from its initial value of about 6.4 g COD/l to a value of about 6.5 g COD/l just after the change in feed rate. It will be seen in FIG. 5 that this change in concentration, amounting at first to less than 2%, caused a substantial and practically immediate change in the rate of production of methane.

We have found it useful to consider the methane production rate in terms of the weight of COD removed as methane per unit volume of the filter per day (hereafter termed "KL" or "kinetic loading" and expressed, like OL, as lbs COD/cu ft/day); one pound of methane has a COD of 4 lbs. Then KL÷OL indicates the methane efficiency of the filter. As seen in FIG. 5 the methane efficiency, so calculated, dropped when the change was made and then rose again; this was due, at least in part, to the method of calculation in that the change resulted immediately in a new, 20% higher OL (the denominator in the efficiency calculation) while the actual immediate increase in COD concentration in the combined stream feed to the filter was less than 5%, as noted above.

Figure 6:
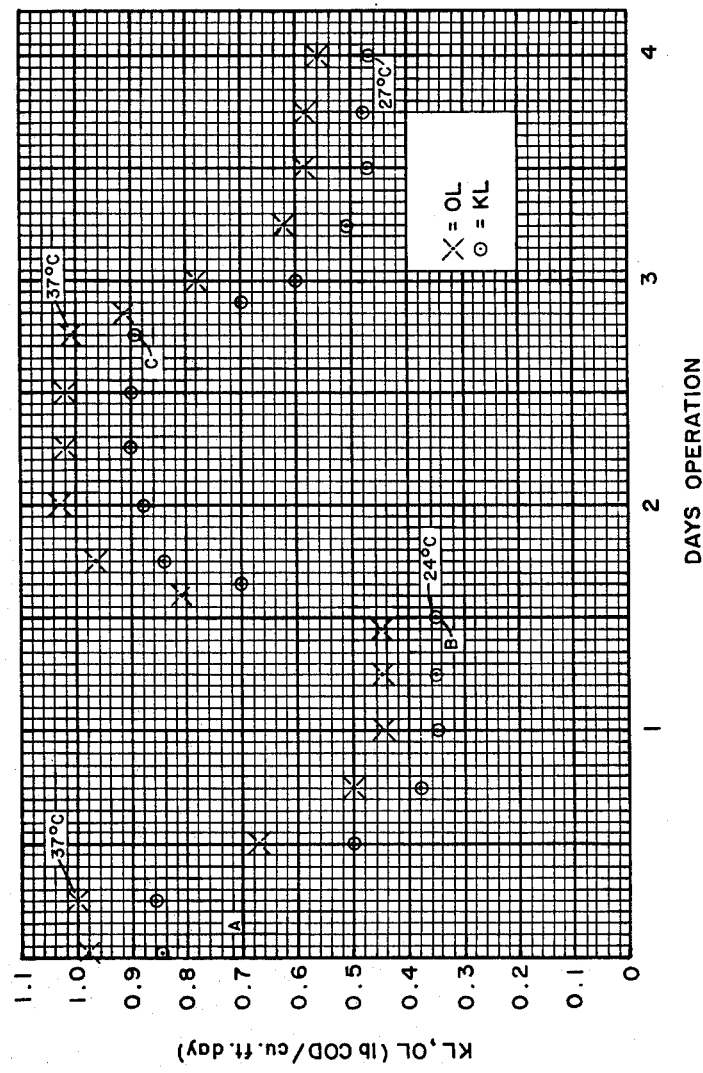
FIG. 6 is a graph showing variations of OL and KL in response to temperature changes in an anaerobic filter controlled to operate at a methane efficiency of 85%.

In accordance with one aspect of this invention, the methane efficiency of the filter is monitored continually and the loading (OL) is changed (e.g. increased) continually to maintain that efficiency at a significantly lower level than that which the anaerobic filter is capable of attaining without such increase in loading. In a preferred form these changes in loading are effected at times substantially less than four hours apart, preferably less than 2 hours apart such as ½, ¼ or 1/12 hour apart; the changes in OL, being made so frequently, are generally each of small magnitude (e.g. less than 10%, but, as seen in FIGS. 6 and 9, the changes are sometimes such that, in a system in which OL is changed once every 6 minutes, the OL may be approximately double in an hour, particularly when the OL is being raised from a relatively low level such as 0.4). By operating in this way, we have been able to increase the OL of anaerobic filters to previously unheard of levels, well over 2 lbs COD/cu ft/day (e.g. to about 3 or 4 lbs COD/cu ft/day or more). We have also been able to effect very rapid increases in the loadings of anaerobic filters which had been operating at comparatively low loadings (such as 0.2 or 0.3 lb COD/cu ft/day), thus making it possible to decrease significantly the time needed to bring a newly installed filter (or a previously damaged or upset filter) to a desired relatively high capacity.

By the use of our novel procedures we have been able to bring the filter relatively rapidly to a previously unknown condition in which the volume of biomass in the filter occupies a major portion of the void volume of the filter. Previously, the known filters had only minor proportions (by volume) of biomass; for instance the previously mentioned Witt et al application says:

"In the operation of the anaerobic filters it has been found that the amount of biomass adhering to the packing, even after extended operation, is such as to occupy only a small fraction of the void volume of the filter, e.g. some 20% or less of the void volume (this being measured by allowing the contents of the filter to drain out and measuring the volume of the liquid thus removed), even though there is a significant recycle of biomass to the filter. While the reasons for this are not clearly understood, it is believed that the recycled bacterial serve, in part, as food for the bacteria in the filter. It is also found, on inspection of filters after lengthy (e.g. 6 months or more) operation under recycle that the biomass attached to the filter packing is distributed on the packing substantially throughout the filter, visually this distribution appears to be substantially uniform from top to bottom. The biomass is gelatinous or slimy . . . "

Along somewhat similar lines is discussion by Lovan & Foree in an article entitled "The Anaerobic Filter for the Treatment of Brewery Press Liquor Waste" in The Brewers Digest February 1972 pages 66–73; this describes experiments using anaerobic filters six feet high having an unpacked volume of 33.4 liters and a void volume (as packed) of 15.2 liters; it states (at page 72):

"After 100 days of operation significant biological solids had accumulated to a depth of about 12 inches in Filter 1 and about 24 inches in Filter 2".

In contrast, with our procedures we have operated anaerobic filters such that, on draining, the amount of free (drained) liquid is well below 70% of the void volume, such as 10, 20, 30 or 50% of the void volume, including filters of such high biomass content that on draining it was found that their packing rings (and even their recycle lines) were almost completely filled with gelatinous biomass. One would have expected that such filters would not operate well in that there would be great interference with the flow of liquid through the filter, causing a decreased capacity, but that expectation has been found to be incorrect, since these filters operate very well and with little back pressure and little, if any, more discharge of biomass and at unusually high loadings. They have, in addition, extremely good resistance to damaging upsets that would put ordinary anaerobic filters out of commission. The reasons for this are not understood. it is believed that the large bodies of biomass may be highly permeable to the organic compounds in the water and this may be due to the presence of a gel type of secretion surrounding individual bacteria or groups (e.g. layers) of bacteria, which secretion is permeable to those organic compounds thereby somehow giving the bacteria in the interior of these bodies of biomass access to the food represented by those compounds. The manner in which the liquid moves through such filters is not clearly understood. It is possible that it flows through a network of fissures and channels. Upward flow of liquid is aided by the percolation effect of the relatively large evolution of gas bubbles in the filter and it appears that there is a high degree of backmixing within the filter. Thus, in a tracer experiment in which a small slug of India ink was injected into the liquid flowing (at a rate of about 240 ml per minute) into the base of a cylindrical recycling filter (having a diameter of 6 inches, a void volume of about 20 liters and a height of 4 feet), the effluent from the top of the filter was dark about 10 minutes after the injection (i.e. after a total flow of some 2.4 l) and very black when observed 15 minutes after the injection (a total flow of some 3.6 l). The flow rate of about 240 ml per minute through the filter (cross sectional area about 180 cm$^2$) corresponded to an average flow rate (across the whole cross-section) of only 1.33 cm/min, but the ink reached the top at a rate of over 12 cm/min. It is possible that, despite the fact that the structure of the gelatinous biomass is strong enough to bridge the spaces of 1 inch diameter Pall rings, and despite the very low pressures in the anaerobic filter, the biomass may become broken up into smaller flowable aggregates under the influence of the flows of liquid and gas during operation of these filters of high biomass content.

A paper by Bellegem et al on "The Anaerobic treatment of waste water of the potato starch industry" in December 1974 issue of TNO Project states that:

"It is clear that with an anaerobic filter the major object is to reach a concentration of biomass that is as high as possible because this will increase the stability, the efficiency and the capacity of the system".

In speaking of the highest attainable capacity those authors said:

"In our experiments it appeared that a load of about 8 kg COD/m$^3$/day could be maintained continuously, but that higher loads can lead to process instability and failure".

This OL of 8 kg COD/m$^3$/day corresponds to only 0.5 lb COD/cu ft/day and is thus much less than the OL levels attained by the use of our invention.

In the large bodies of biomass attached to the packing it seems likely that there is a gradient in concentration of the components of the feed solution from the outer portions of each such body of biomass to its interior. This may be as a result of diffusion through a gelatinous secretion that is permeable to such components. The outer portions of each such body may be in contact with the relatively concentrated mixture of recycled material and free feed; when the concentration in that mixture reaches an inhibitory or toxic level, the bacteria in the outer portions may be adversely affected owing to exposure to that concentration while interior bacteria may continue operating more or less as before because the concentrations to which they are exposed are significantly lower than those in the outer portions. This may help explain the increased resistance of the filters to upsets.

Figure 2:
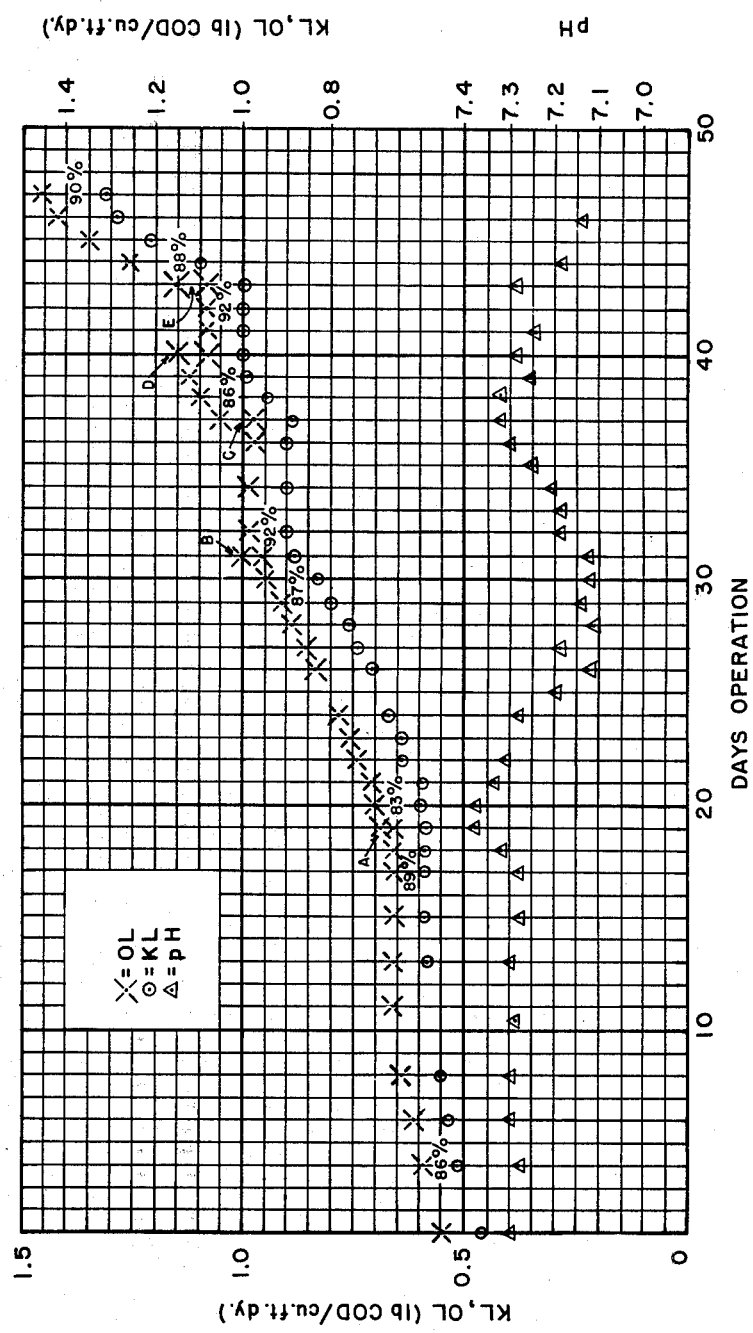
Figure 3:
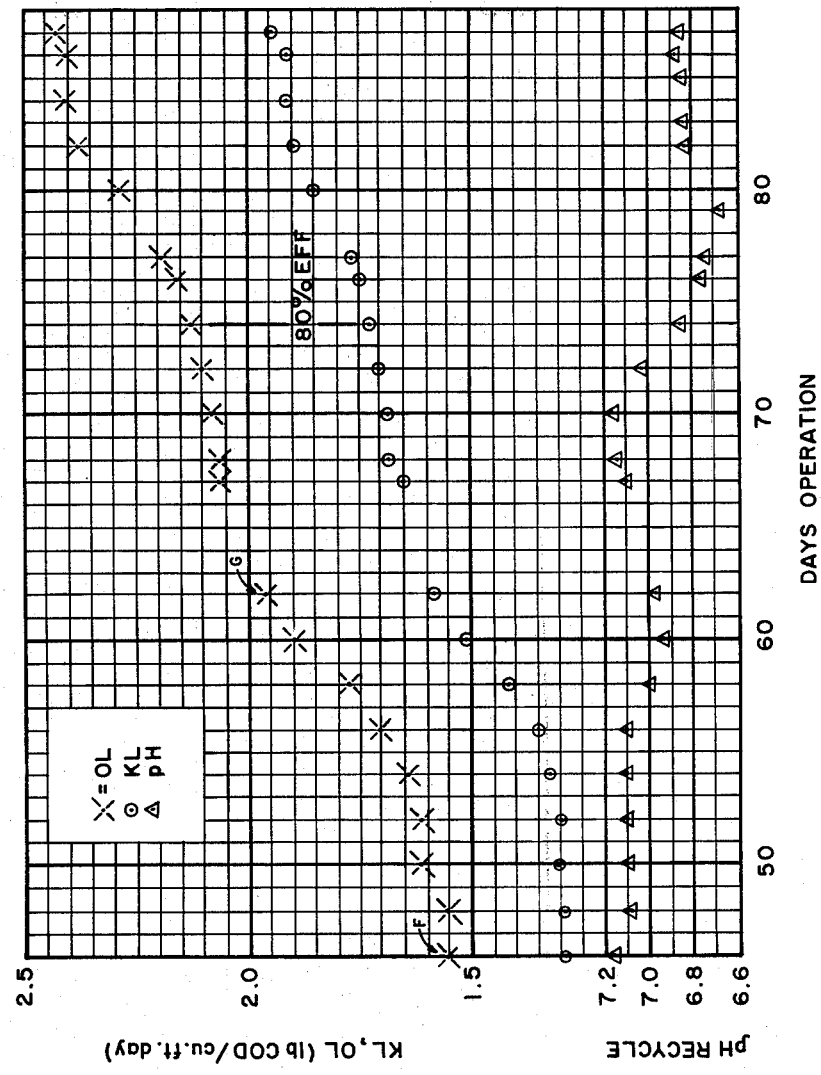

It may be that the rapid increase in loading observed when this invention is employed can be explained as follows. The amount of "food" for the bacteria is maintained at a controlled high concentration which promotes growth of the bacterial population, but is always kept below an inhibitory concentration. (The concentration which cause inhibition depends on the particular compound; methanol does not become inhibitory until its concentration is relatively high; the inhibitory concentration is lower for acetic acid than for methanol; for acrylic acid it is much lower). FIG. 2 (taken with Example 1) indicates that, with a feed containing 15 g COD/l, growth was promoted when the efficiency was set at 87 or 88% but was not promoted during a 4-day period when the efficiency was set at 92%. At the 88% efficiency, with this feed, the COD concentration prevailing in most of the recycling filter would be about 1.8 g COD/l, (i.e. 12% of 15 g COD/l) while at the 92% efficiency it would be only about 1.2 g COD/l. When the efficiency was 80%, as illustrated in FIG. 3, the COD concentration in the filter would be even higher (i.e. about 3 g COD/l for the 15 g COD/l feed and about 5 g COD/l for the 25 g COD/l feed) but it was still not high enough to cause this feed (which contained formaldehyde and acrylic acid in significant amounts) to have a significant inhibitory effect on the action of the large amount of biomass that has built up in the filter, as can be seen from the results shown in FIG. 3.

The Examples, below, are given to illustrate the invention further.

Figure 1:
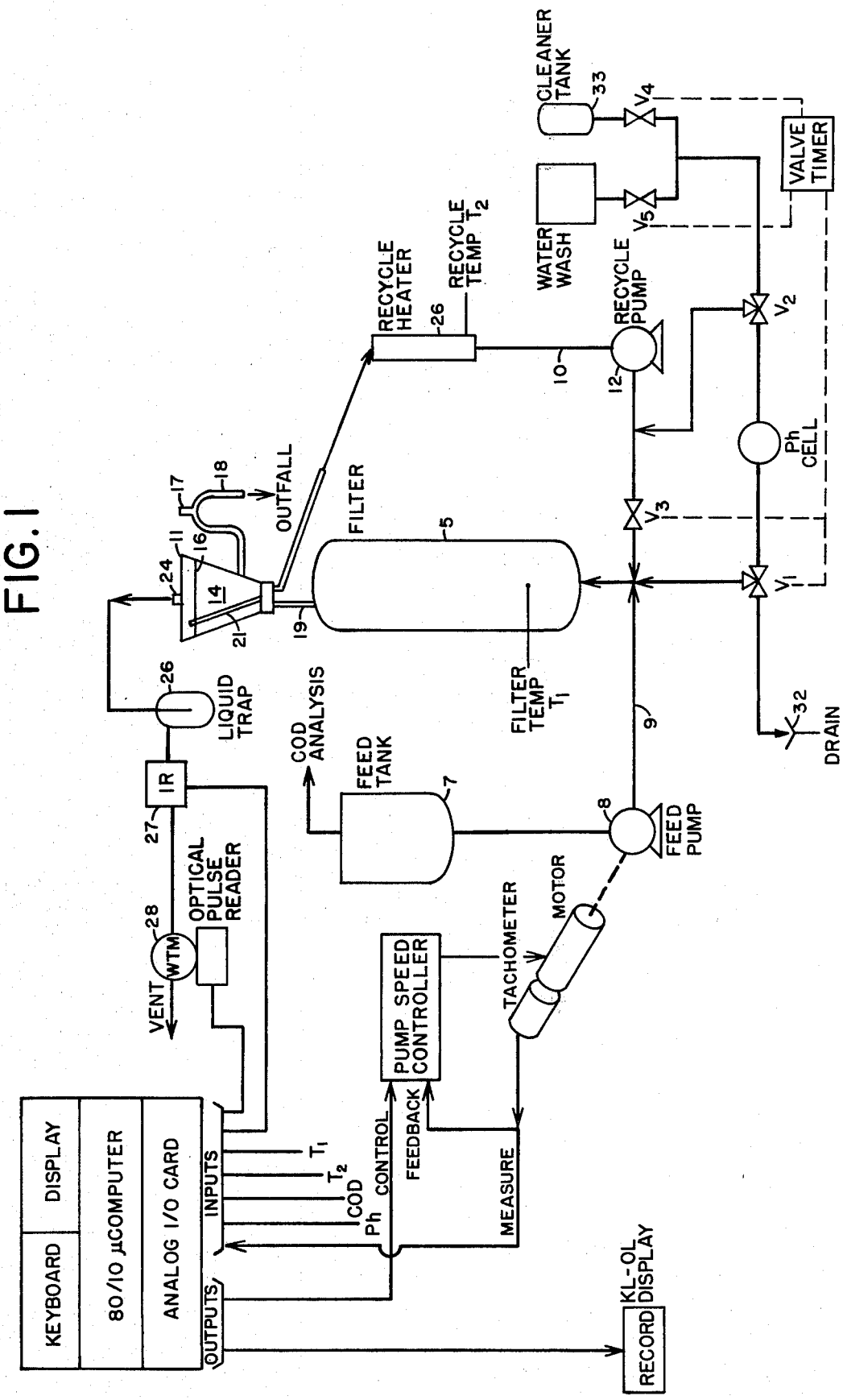

In Examples 1-5 below the anaerobic filter was a circular cylindrical corrosion resistant tank 5 (FIG. 1). The tank was 4 feet high and 6 inches in diameter and was filled with randomly arranged plastic rings (Pall rings plastic biorings, one inch in diameter, 1 inch high). This packing provided a surface area of 50 sq. ft/cu ft and a void space of 90%. The packing rings were of polypropylene plastic having a density of about 0.9, so that they tended to float in the liquid contained in the tank and contacted the upper wall of the tank, and there was free, unpacked, space at the bottom of the tank; more specifically about 2 inches above the bottom of tank 5 there was a horizontal screen; the zone below the screen did not contain packing. The total volume of the tank was 22.2 l without packing; as packed its void volume was 20 l. The acidic waste supplied to the anaerobic filter was fed from a feed tank 7 by a positive displacement pump 8 (having a speed controlled motor), through a pipe 9 into a stream of recycled liquid effluent, with bacterial solids, flowing in recycle loop 10 from a disengagement vessel 11 at the top of the filter and drawn by a recycle pump 12. The combined feed and recycle stream entered the bottom of the tank, below the horizontal screen, through a ⅜ inch diameter central opening. Just upstream of the point of entry into the tank there was a check valve (not shown) which acted as a safeguard to prevent the contents of the tank 5 from draining out in the event of a rupture of a pipe.

Liquid and gas emerged from the top of the tank 5 (through a central pipe having a diameter of ⅜ inch) and flowed into disengagement vessel 11 in which there was a body of substantially quiescent liquid 14 whose surface 16 was maintained at a substantially constant level by the presence of an overflow seal 17 of the inverted syphon type in an outfall line 18. The liquid-gas mixture from the tank 5 flowed upward through a tube 19 whose outlet 21 was above the surface 16 (such as 1 to 2 inches above it). This liquid-gas mixture contained also solid biomass material, mainly in finely dispersed suspended condition but also containing some larger particles of solid biomass material, which particles may be loosely attached to bubbles of the gas. On spilling out from the narrow tube 19 (a circular tube ⅜ inch in diameter) such gas bubbles tended to be released from these larger particles (which are flocculent rounded or spheroidal about 1 to 5 mm in diameter). The latter then settled in the liquid body 14 and were drawn off with the liquid from the bottom of the vessel 11 and returned to the tank 5 through the recycle loop 10. The outfall (non-recycled effluent) which left through seal 17, was often slightly clouded because it contained the finely dispersed biomass material, (e.g. in the range of about 50 to 500 mg VSS/l usually about 200 to 300 mg/l as measured by filtering the liquor through a 0.45 μm membrane, which retains individual organisms). The settling vessel 11 was of such size that the average residence time therein (i.e. rate of flow of liquid, and solid, from tube 19 divided by volume of liquid body 14) was well below 0.2 hour, e.g. 6 minutes. (This residence time was so short that there was substantially no tendency for the settled biomass particles to generate sufficient gas that would float many of them and thus cause them to appear in the outfall). The gas left through a pipe 24 at the top of vessel 11.

There was a heater 26 in recycle loop 10 for warming the recyclng material to the optimum temperature.

In the Examples the vessel 11 was of inverted conical shape containing about 8 inches of liquid and 3 inches of free gas space above it. The level of upper liquid surface 16 was about one foot above the top of the tank 5. The void space above the surface 16 was at atmospheric pressure or slightly above.

The volumetric rate of feed through pump 8 (which was of the positive displacement type) was measured continuously (by means of a tachometer sending an electrical signal proportional to the pump speed, and hence proportional to the liquid flow.) The vent gas leaving through pipe 24 passed through a conventional demister 26 and then was analyzed continuously by passing it through a standard infrared methane analyzer 27 and then through a wet test meter 28.

The methane analyzer was a Beckman infrared analyzer (Model 865) of a type well known in the art, using a detector filled with methane. The instrument was calibrated regularly so that its electrical output was linearly proportional to the methane concentration of the vent gas.

The wet test meter 28 was fitted with an optical detector and a 250 tooth gear designed to produce 250 electrical pulses for each liter revolution of the meter.

The outputs of the wet test meter and $CH_4$ analyzer were combined (by suitable instrumentation) to give an electrical signal indicating the rate of methane production (and thus of the "kinetic loading" or "KL"). This can be expressed as the number of pounds of COD in the form of methane per unit of the time per unit volume of the filter (one pound of methane has a COD of 4 lbs.).

The output signal for pump feed rate was combined with the known (or regularly measured) COD level of the feed to give an electrical signal indicative of the COD feed rate and thus of the OL.

The motor driving the positive displacement feed pump 8 was controlled by a controller including a calculating processing unit or microprocessor (described hereafter) to maintain the OL in a predetermined relationship to the KL.

Other instrumentation included thermocouples to sense the temperatures at (a) the geometric center of the filter and (b) in the material being recycled, as well as a pH meter to measure the pH of the recycled liquid just upstream of the point where the fresh feed was introduced into it.

EXAMPLE 1

The acidic waste used in this Example 1 was a water solution containing a mixture of the following:
- 375 parts acetic acid
- 37.5 parts formaldehyde
- 115 parts formic acid
- 44 parts butyric acid
- 30 parts of acrylic acid At the start of the run the concentrations of these ingredients were such that the level of COD was 15 grams per liter, so that the concentrations were as follows:

| | |
|---|---|
| acetic acid | 9.38 g/l ≡ 10 g COD/l |
| 100% formaldehyde | 0.94 g/l ≡ 1 g COD/l |
| formic acid | 2.88 g/l ≡ 1 g COD/l |
| butyric acid | 1.10 g/l ≡ 2 g COD/l |
| acrylic acid | 0.75 g/l ≡ 1 g COD/l |

Later in the run the feed was made more concentrated (without changing the ratios of the ingredients) so that the level of COD was 25 g/l; thus the concentrations were as follows:

| | |
|---|---|
| acetic acid | 15.63 g/l ≡ 16.67 g COD/l |
| 100% formaldehyde | 1.56 g/l ≡ 1.67 g COD/l |
| formic acid | 4.79 g/l ≡ 1.67 g COD/l |
| butyric acid | 1.8 g/l ≡ 3.33 g COD/l |
| acrylic acid | 1.25 g/l ≡ 1.67 g COD/l |

In addition, for each 24 liters of water the feed mixture contained 6.3 grams of urea, 2.2 grams of 85% phosphoric acid (the concentrations being such that the COD:N:P ratio was 1000:5:1), 24 ml of an aqueous solution comprising ferrous and cobaltous sulfates (containing 1 mg/l of each of $Fe^{++}$ and $Co^{++}$) and 24 ml of an aqueous solution of sodium sulfate (concentration of S in that solution was 10 mg/l) and 8 g/l of Na $HCO_3$. These feed mixtures were acidic; their pHs were probably in the neighborhood of 4 to 5.

At the beginning of this run the filter had already been started and had operated for about 2½ months with the same feed mixture (COD level, 15 g/l), and the rate of feed of acidic waste was such as to provide a loading (OL) of about one half pound COD per cubic foot per day (calculated on the basis of the 20 l void volume of the tank).

The progress of the run is shown graphically in FIGS. 2 and 3.

At the outset of the run the controller was set to maintain a substantially constant difference ("ΔL"), of about 0.08 lbs COD per cubic foot per day, between OL and KL. That is, when KL+0.08>OL, the controller increased the feed rate to raise the OL so as to maintain the desired difference; and vice versa. At the outset, the 0.08 figure corresponded to an efficiency of about 86% (i.e. KL/OL=0.86) based on the value of OL at the outset. Over a 16 day period of operation under these conditions the KL rose to almost 0.6 and the efficiency rose to about 89%. In the next few days the KL (and, of course, the OL) decreased slightly.

The controller was then (at point A on the graph) set to give a ΔL of 0.12 lbs/cu ft/day. Initially this corresponded to an efficiency of 83%. As can be seen from the graph, within some 11 days of the change, the KL had increased to about 0.9 and the efficiency had risen to 87%.

The controller was then (at point B on the graph) reset to give a ΔL of 0.08, corresponding, at that point, to an efficiency of 92%. As shown in the graph, the KL remained substantially constant for the ensuing 4 day period.

Next, the controller was (at point C on the graph) reset to give a ΔL of 0.16, corresponding at that point to an efficiency of about 86%. This resulted in a marked increase in KL, to about 1.0 lb/cu.ft./day, in a few days.

At point D the controller was re-set to give a ΔL of 0.09, raising the efficiency to 92%, and the KL stayed substantially constant. At point E the controller was again re-set to give a ΔL of 0.15, corresponding at that point to an efficiency of about 88%; within a few days the KL was over 1.4 and the efficiency was about 90%.

At point F (FIG. 3) the controller was set to give an efficiency of about 80%. That is, the KL:OL ratio was maintained at about 80% (allowing ΔL to vary accordingly, i.e., KL/OL=(OL−ΔL)/OL=0.80; so that ΔL=0.20·OL)

At point G the feed was made more concentrated; that is, the fresh feed to the filter was the feed solution containing 25 g COD per liter instead of the previously employed solution of 15 gCOD/l. The efficiency was maintained at 80%. Within a little over a month after the 80% efficiency control scheme was adopted the KL had risen to almost 2.0 and the OL was over 2.4; these were levels never before attained.

During the run the recycle pump was driven at a substantially constant speed to supply 12 liters per hour of recycled material. Since the rate at which fresh feed was supplied was changed during that period, the recycle ratio changed as indicated below:

| | Feed Rate ml/hr | Recycle Ratio |
|---|---|---|
| start February | 480 | 25:1 |
| point A* | 620 | 19.4:1 |
| point B* | 889 | 13.5:1 |
| point C* | 940 | 12.8:1 |
| point D* | 967 | 12.4:1 |
| point E* | 1030 | 11.7:1 |
| point F* | 1329 | 9:1 |
| point G* | 994.3 (richer) | 12.1:1 |
| End* | 1286 (richer) | 9.3:1 |

The average upward flow rate (across the entire 180 $cm^2$ cross section of the filter) can be readily calculated from the feed rates and the 12 l/hr recycle rate; in each case it was not much greater than 1 cm per minute.

FIG. 2 indicates that when ΔL was too low (or when the set efficiency was too high) growth did not occur. In FIG. 3 ΔL was above that low level and gave an unprecedented growth to an OL of 2.4 and a KL of almost 2.

EXAMPLE 2

The run described in Example 1 was then varied by feeding a different feed solution to the same apparatus containing the same biomass. This new feed solution contained the water-diluted waste effluent of a plant manufacturing acrolein, acrylic acid and acrylate esters. From time to time, the feed strength varied in the range of about 25 to 35 g COD/l, on the average its strength was about to 30 g COD/l, of which roughly 10 g COD/l was from acrylic acid and 8–10 g COD/l was from acetic acid, other components being ethanol, ethyl acetate, ethyl acrylate, diethyl ether (low level), butanol, butyl acetate, secbutyl acrylate, n-butyl acrylate, and some acrylate low polymers.

In the course of this Example the efficiencies were set at different levels in the range of roughly 65–75% and OL values of well over 2 (such as 2.5) lbs. COD/cu ft/day and KL values such as 1.8 (or 1.9 or more) lbs. COD/cu ft/day were attained.

During one period the controller acted to reduce the OL to about 0.2. It was found that the feed solution used during that period contained significant amounts of a toxic component (chloroaldehyde). The filter was then flushed with water containing 2 g/l NaHCO$_3$ and then a feed solution substantially free of that toxic component was fed to the filter at a fixed rate to supply an OL of about 0.74 over a period of 5 days, during which time the KL rose from 0.52 to 0.6 (showing a gradual increase in efficiency to about 80%). Then the feed rate was put under the control of the automatic controller, the efficiency being set at 75%; the KL rose to over 1.0, and the OL increased to over 1.3, within about 16 hours, as shown in FIG. 8.

Over the course of this Example the KL rose at one time to 2.4 and the OL to 3.5. Some mechanical difficulties then occurred (as described below) and after a few more weeks the tank 5 was allowed to drain by gravity. Only 1.8 liters of liquid drained out of the tank, even though its original void volume was 20 liters.

The 1.8 liters of drained liquor were retained (in an open vessel, exposed to air) for use in Example 3. It contained considerable suspended biomass. Dumping of the packing of the tank showed that the rings and recycle lines and other portions of the unit were almost completely filled with biomass. The original total weight of the packing rings was about 4.35 pounds, while the weight of the dumped rings containing biomass was 36.50 pounds, showing that the rings carried 32.15 pounds of biomass. Drying the biomass at 115° C., a procedure which removes the "free" or extracellular moisture surrounding the bacterial cells, indicates that this "free" water constituted about 89.5% of the biomass adhering to the rings. The dried weight of the biomass (dried at 115° C.) was 3.376 pounds; calcining (at 600° C.) gave an ash in amount of 23.1% of the dried weight; qualitative analysis of the ash (by atomic absorption) showed the presence of iron and minor amounts of copper and zinc.

The rings filled with biomass floated when placed in water; their overall density was slightly less than that of water. The biomass could be removed easily from the rings, as by agitation in water.

With respect to the mechanical difficulties mentioned above, after the KL had risen to 2.4 and the OL to 3.5, a mechanical defect caused a drain line to split so that all the liquid drained from the filter. The filter was refilled and within a few days was operating at a KL of 1.8 and an OL of 2.7 (efficiency was set at about 66%). The KL began to drop thereafter, with a corresponding decrease of OL so that in a few weeks the KL was about 1.2 and the OL was about 1.8. Inspection showed that a vent of the wet test meter had somehow become plugged so that that meter was transmitting readings of rate of gas formation that were significantly lower than the true rates; as a result, the controller had been lowering the feed rate accordingly. At this time the tank was allowed to drain, as described above.

It should be noted that in this Example the action of the controller protected the filter from the effects of an unforeseen high toxicity of the feed and make it possible for the filter to remain in a condition in which it could resume operation and attain high loadings quickly with feedstock which did not contain dangerous levels of the toxic component.

EXAMPLE 3

After the run in Example 2, almost all the biomass was removed from the rings, which were then returned to tank 5. The tank was filled with the 1.8 liters of drained liquor from Example 2 together with water containing a total (for the whole refill) of 50 g of methanol and 30 grams of sodium acetate and the apparatus was operated at 100% recycle with no fresh feed until an operational temperature of 37° C. was attained. Thereafter the fresh feed was a 90:10 blend of water and the previously mentioned 30 g COD/l diluted effluent (used in Example 2), for two days; then a similar, but 80:10, blend for one day; and then the fresh feed was changed to be solely the previously mentioned 30 g COD/l diluted effluent (containing 8 g/l of added NaHCO$_3$). The controller was set to give an efficiency of about 70% beginning at an initial feed rate corresponding to an OL of about 0.25 (expressed, as usual, as lbs. COD/cu ft/day). Within three weeks the OL had risen to about 2.9 and the KL to about 2 lbs. COD/cu ft/day. The efficiency was then set at 75% for about 5 days, then at 80% for a day and at 85% for another day; the KL was still about 2 lbs. COD/cu ft/day. The efficiency was then set at 90% and the KL dropped to about 1.8. The unit was then drained; 12.9 liters of liquor were obtained (compared to the total void volume of 20 liters in the absence of biomass).

In this Example, starting with a relatively small amount of biomass that had been acclimated to the same type of feed, the use of the controller caused a rapid rise in KL to a level of about 2 and then caused a rapid rise in efficiency while retaining this high KL.

EXAMPLE 4

Figure 4:
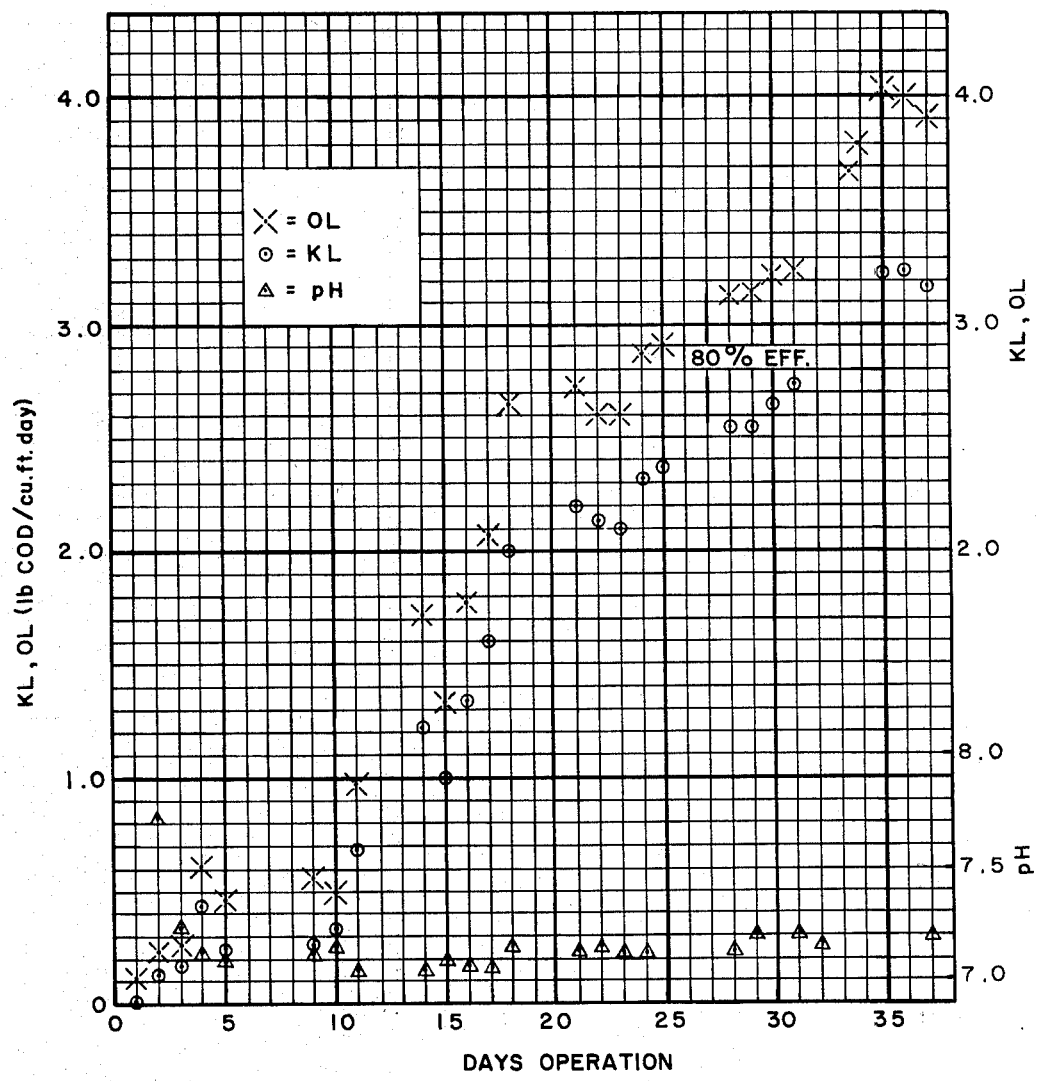

After the draining described at the end of Example 3 the unit was re-filled with water containing 2 g/l NaHCO$_3$ and kept at 100% recycle (no feed) overnight to reach a temperature of 37° C. It will be understood that during the period (about an hour) between draining and refilling the anaerobic biomass in the unit was exposed to the air. The fresh feed was then changed to an aqueous mixture containing equal COD loadings of each of four different C$_4$ organic compounds; n-butanol, sec-butanol, n-butyraldehyde and n-butyric acid. This mixture was diluted with water as needed to provide a feed stream of the strengths (expressed as g COD/l) tabulated below. For instance to provide a feed strength of 20 g COD/l the mixture contained 1.93 g/l n-butanol; 1.93 g/l sec-butanol; 2.05 g/l n-butyraldehyde; 2.75 g/l of n-butyric acid, providing 5 COD/l of each component. The fresh feed also contained 4 g/l of NaHCO₃. FIG. 4 shows the results graphically. It will be seen that the KL rose, within about a month, to over 3.2 while the OL was about 4 lb COD/cu ft/day.

| Day | Feed Strength | Set Efficiency % |
| --- | --- | --- |
| 1 | 2.0 | 10 |
| 2 | 2.0 | 50 |
| 3 | 5.0 | 65 |
| 4 | 5 | 65 |
| 5 | 10 | 50 |
| 6,7,8 | | |
| 9 | 10 | 40 |
| 10 | 10 | 65 |
| 11 | 20 | 70 |
| 14 | 20 | 70 |
| 15 | 30 | 75 |
| 16 | 30 | 75 |
| 17 | 30 | 75 |
| 18 | 30 | 75 |
| 21 | 30 | 80 |
| 22 | 30 | 80 |
| 23 | 30 | 80 |
| 24 | 30 | 80 |
| 25 | 30 | 80 |
| 28 | 30 | 80 |
| 29 | 30 | 80 |
| 30 | 30 | 80 |
| 31 | 30 | 80 |
| 35 | 30 | 80 |
| 36 | 30 | 80 |
| 37 | 30 | 80 |

Notes:
At day 15 a single charge of some activated sludge (from an aerobic process) was added to the feed, to provide an additional population of bacteria.
The data in this table and the OL, KL and pH values shown in FIGS. 2 3 and 4 are not averaged values or settings for the days in question. They are numbers taken once (usually at about 8 AM) during each day; the KL numbers are one hour moving averages as explained below.

There were some mishaps during this period. At day 5 it was discovered that the wet test meter had been leaking so that the information on gas production rate (and thus KL) fed to the controller was less than the true rate. At days 22 and 25 it was found that the clock in the instrumentation (discussed below) had not operated properly, so that the information on KL fed to the controller was again lower than the true value; the effect of this is seen in the depressions of the OL and KL curves in FIG. 4 at 22-24. On day 37 the filter was operating at an OL of 3.9, the set efficiency being 80%; the efficiency setting was raised to about 85%. As can be seen from FIG. 7 at "X"), this meant that the OL was dropped to about 3.7, which in turn caused a drop in KL, and the OL and KL continued to decline. After a day of operation at the 85% set efficiency the efficiency setting was restored to 80% and the KL (and OL) increased at a very high rate, and may have attained levels even higher than would have been projected (from the slopes of the OL and KL curves) had the efficiency been continued at 80% without the 85% one day interlude. At this time the feed line became plugged and the feed pump forced air into the filter for a period of some 11 hours; during this period the automatic controller acted to reduce the OL to about 1.3 in one hour, to about 0.9 in the next hour and eventually to about 0.28. On repair of the defect the automatic controller acted to raise the OL and KL rapidly; within 12 hours the KL had risen to over 2.4 and the OL to 3.1. The performance of the filter during this period is shown in FIG. 7A.

In this Example 4 the filter (still containing a relatively large amount of biomass which had, however, been exposed to the air) was subject to a different feed; the use of the controller enabled it to attain a very high loading in a short time.

EXAMPLE 5

Example 4 was continued except that the NaHCO₃ level in the feed was lowered to 2 g/l (from the 4 g/l in Example 4). The OL at the start was 3.9 and the KL was about 3.1. The efficiency was set at 80% for a day, then at 81% for 2 kdays and then at 83% for 3 more days, at the end of which time the OL was about 3.9 and the KL was over 3.3 even though the pH of the filter outflow and recycle stream had dropped from 7.1 to 6.4. Thereafter the KL dropped and the efficiency was set at 80% so that within about 2 more weeks the KL was at about 2.1 and the OL at about 2.6 while the pH had fallen to about 6. Due to equipment problems the feed was shut off for about 3½ days while recycling continued. Then the automatic controller was again activated to control the feed rate, using first an efficiency of about 50% for a few hours and then an efficiency of 81%, then 70%; as shown in FIG. 9 the KL and OL rose rapidly and (after 34 hours) reached about 2.1 and 2.9 respectively, even though the pH was still low, about 6.

EXAMPLE 6

The outfall from the filter in Examples 2 and 3 was fed, without further treatment (except as noted below) to a second anaerobic filter operated without controls (except as noted below). This second filter was of the same size and shape as the first one. The strength of the feed to the second filter (substantially the same as the strength of the outfall from the first one) during this period ranged from about 1 g COD/l (at the time when the first filter was being operated at a fixed rate of feed, illustrated in FIG. 8) to about 7 g COD/l (e.g., at the time when the OL of the first filter was rising to well over 3). The volumetric feed rate and OL of the second filter are of course dependent on the feed rate and OL on the first filter; during this period the volumetric feed rate on the second filter ranged from about 0.33 liter per hour to about 1 liter per hour and the OL on the second filter ranged from about 0.03 to about 0.52 lb COD/cu ft/day.

The overall % removal of COD (based on COD content of feed to first filter) as a result of passage through the two filters ranged from over 89% to over 98%, being at about 95% or more for most of the period.

In this Example the two filters were in different rooms and the outfall from the first filter was collected each day and then fed to the second filter on the next day. During this one-day wait the outfall cooled down; to maintain the second filter at a temperature of about 37° C. it was operated with recycling, in order to make use of a recycle heater (whose position was as shown in FIG. 1). (In a commercial installation the warm outfall from the first filter would be fed directly to the bottom of the second filter with no need for reheating or temperature control and no need for recycling; thus the second filter would be operated under plug flow conditions and could be made considerably smaller than the first filter.) During the one-day wait the surface of the collected outfall was exposed to the atmosphere (before feeding it to the second filter) resulting in a loss of CO₂ and a rise in pH (to about 8); as a result the methane concentration in the gas produced by the second filter was relatively high, in the neighborhood of 90%.

The controller may be a microprocessor (an Intel System 80/10 Microcomputer), coupled with programmable digital input/output devices (two Intel Silicon Gate MOS 8255 Programmable Peripheral Interfaces) and an "analog" input-output card (an Analog Devices RTI-1200 Real-Time Interface). The latter card receives analog signals from the sensors, converts them into digital signals and transmits them to the input of the microprocessor; it also receives digital signals from the output of the microprocessor and converts them to analog signals. More particularly the input-output card provides the following: 32 Analog inputs single ended (or 16 inputs double ended), 2 Analog outputs, 2 Logic driver outputs, 2 Real Time Pacer Clocks, 1 K bytes of memory. Six of the Analog inputs are used. The two analog outputs are used to drive a recorder and to control the feed pump 8. The logic drivers are used to alarm for low pH and high temperature. The Pacer Clock is used to count cycle time (60 minutes), trigger data logging every 30 seconds and start calculations and control changes every six minutes. The one Kilobyte of memory is part of the total 5 K memory for the microprocessor-based controller.

The microprocessor is programmed so that the output of each sensor (the wet test meter, the methane analyzer and the tachometer attached to the motor of feed pump 8, as well as others discussed below) is automatically received, or logged, once every 30 seconds, and so that a series of values of each or the variables (namely rate of gas production, methane content of gas and feed rate, and others) is stored in the controller. The microprocessor program is such that every 6 minutes, the controller (a) calculates the average of each of these variables (for the past 6 minutes); (b) calculates the average KL for the past 6 minutes (from the value of rates of gas production and methane contents); (c) calculates the average OL for the past 6 minutes (from the values of feed rate and from the value of the strength of the feed, the latter value having been put into the controller manually through its keyboard); (d) calculates the average KL for the past hour; (e) calculates the relationship between the values of c and d (e.g. the % efficiency); (f) calculates the OL (and corresponding feed pump speed) needed to maintain the pre-set relationship between the values of c and d; and (g) sends an electrical signal to the speed control of the feed pump motor to establish a new value of OL.

The reason for using a one-hour average of KL is to avoid, or smooth out, the influence of very short term variations which will not indicate the true KL. Thus, vibration or shaking of the anaerobic filter may cause a momentary extra release of gas; similarly, occasionally some of the gas being formed in the filter may accumulate in a localized packed area (forming a "pocket" of gas) and then be suddenly released so that the unit may be said to "burp". Individual measurements made during such periods will, of course, not reflect the actual rate of gas production.

It will be understood that the term "average" is used here in the broad sense, since it will be clear to those skilled in the art that one may use any value proportional to the average, so long as the same proportioning factor is applied to other significant variable or built into the responses. For instance, since the instrument logs 120 values of methane content and 120 values of gas production rate in an hour, the controller may use (as its calculated "average" KL in carrying out operation e above) the sum of the 120 individual methane production rates (obtained during the preceding hour) or the equivalent of that sum expressed as KL, and the controller may compare that sum with 10 times the sum of the 12 individual OLs (obtained during the preceding 6 minutes).

In the foregoing description, the strength of the feed is logged manually into the controller, based on an analysis (e.g. daily) of the COD level of the feed. It will be understood that better control may be obtained by making the feed COD analysis more frequently and logging the COD value into the controller at correspondingly shorter intervals, and that this may be done by an automated COD analyzer (or commercially available TOD analyzer) taking samples from the feed tank.

Among the other signals fed at intervals to the microprocessor is a signal indicating the value of the pH. This signal is preferably generated by a pH meter (Great Lakes Instruments Inc. Model P60L-2-1 pH probe) having two matching glass electrodes. (One electrode is used as the reference and is submerged in a pH 7 buffer). Its electrical circuit is such as to give zero output when the solution being tested (in contact with the non-reference glass electrode) is at pH 7 and to give a positive or negative output when the pH is, respectively, above or below 7. The pH cell is subjected, each hour, to a cycle of: (a) rinsing with water under pressure (e.g. 30 psig) for about 2 minutes to detach loose solids and drain gas bubbles from the portions that have been exposed to the biomass-containing liquid being recycled; (b) exposure for 38 minutes to a cleaning solution which is mildly acidic to remove carbonates and contains detergent (e.g. Alconox) to remove greasy films and a bactericide such as hydrogen peroxide to kill live organisms that may still be present at significant points (the hydrogen peroxide-containing cleaning solution preferably contains an agent, such as EDTA, to complex metals that may cause decomposition of the hydrogen peroxide); (c) exposure for another two minutes to the water rinse; and then (d) exposure for 18 minutes to the recycle stream. These successive exposures are effected by a system of valves V1, V2, V3, V4 and V5 (FIG. 1), controlled by a valve timer 31. For the first 42 minutes of the cycle, V3 is open; for the next 18 minutes (step d above) it is closed. During the water rinsing steps (a and c above) V5 is open and V1, V2 are in a position to permit flow from the water supply through the pH cell to the drain 32. At the outset of the cleaning step (b above) V4 is open and V1 and V2 are in a position to permit flow from the cleaner tank 33 through the pH cell to the drain; then the valves are closed and the pH cell remains filled with stationary cleaning buffer solution. The buffer solution contains NaOH and $H_3PO_4$ in such proportions that its pH is 6.2; this serves as an aid to check the calibration of the instrument in that the pH measured by the instrument is displayed in the usual fashion at all times and the operator can check to see whether the displayed pH is 6.2 during step b. For the last 18 minutes (step d) the cleaned and rinsed pH cell is exposed to the circulating recycle solution (by closing V3 and turning V1 and V2 to positions permitting the solution to flow through V1, the pH cell and V2 and back to the point where it meets the feed solution). The arrangement is such that the output of the pH meter is logged (transmitted to the controller) only during the later part of step d; this may be done by the timer which controls the valves, i.e. that timer may close the electrical connection to the controller only during the last 10 minutes of step d, and keep it open at all other times.

During those ten minutes, the controller may log the pH once every 30 seconds, as is done with the signals from other sensors.

The pH indicates the balance between acid-forming and acid-consuming (methanogenic) bacteria and may be used for control together with KL. Thus, the controller is programmed to operate a light (or other alarm) indicating "low pH" when the pH drops to one predetermined level (say pH 6.8) and to shut off the feed pump motor when the pH drops to a predetermined lower level (say pH 6.2). When the feed pump is thus shut off the recycle pump continues to operate; we have found that during this period the methane-forming bacteria will gradually consume the excess volatile fatty acids and will generate methane (while the fatty acid-forming bacteria will have no new sources of food from which to create new supplies of volatile fatty acids) and the pH will rise. The controller is programmed to have a deadband (extending from say pH 6.2 to 6.8); when the pH has risen to a value above the upper level of that deadband the controller will start the feed motor again to feed at a rate determined by the KL of the filter at the time the pH rises above the deadband level.

A more refined pH control strategy that may be employed involves maintaining the pH at an optimum level for the methanogenic bacteria. This can involve (1) pre-setting the controller to maintain an OL such that there is an excess supply of the volatile fatty acids used as "food" by the methanogenic bacteria, e.g., preset the efficiency at about 80% and (2) pre-setting the controller so that if the pH is above an optimum minimum, say above pH 7.05, the controller operates in the regular way, but when the pH drops to that 7.05 (or other) minimum, or lower, the controller maintains a lower OL:KL ratio (or lower ΔL). For instance the controller may be programmed so that when the pH is 7.05 or less the pre-set efficiency is increased by 1% (e.g. to 81% from the previous 80%) for each new pH measurement which is at or below that 7.05 minimum (since, in the scheme described above, the new measurement of pH is made once an hour, the efficiency will be increased by 1% each hour [e.g. to 81% in the first hour, 82% in the second etc.] as long as the pH is at or below the minimum. It will be understood that such an increase in efficiency means that, for a given KL, the OL (e.g. feed rate) will be lower than before.

Another signal which is logged to the microprocessor every 30 seconds is the signal indicating the temperature of the interior of the filter. The controller is programmed to operate a light (or other alarm) indicating "high temperature" when the temperature reaches 42° C. in order to prevent damage to the methanogenic bacteria. The heater in the recycle loop is controlled (e.g. manually, but preferably thermostatically) in response to the temperature in the filter to maintain the interior of the filter at the optimum temperature; a second thermostatic heater control, based on the temperature of the stream leaving the heater, prevents the temperature of the recycle stream from exceeding 42° C. to prevent damage to the bacteria in that stream. A more preferable heating technique is to pass a heat-exchange fluid (e.g. process steam) through heating coils within the filter itself.

As shown in FIG. 6 we have found that the rate of methane production is quite sensitive to changes in temperature. The heater was shut off at time A, and the temperature in the filter was permitted to drop (from the previous value of 37° C.) to ambient temperature. Then at time B the heater was started again. At time C the procedure of shutting off the heater was repeated. During all this time the controller was set to give a feed rate such that the efficiency was 85%.

The wet test meter which measures the volumetric rate of gas production is sensitive to temperature changes. In one arrangement that meter was situated at a location at which the temperature was kept within a narrow range; it was on top of the infrared methane analyzer which radiated heat from its internal heater. In this arrangement the temperature of the wet test meter typically dropped from a day-time temperature of 29° C. to a night-time temperature of about 26° C. When this occurs the meter indicates (for the very same mass rate of flow of gas of the same methane content) that there has been a drop of about 1% in the volumetric rate; the controller therefore drops the OL (feed rate) by about the same percentage. In the Examples described herein, day-to-night temperature variations of that magnitude occurred and thereby slowed down the rate of increase of OL; that is, it is to be expected that by maintaining the temperature of the wet test meter more constant the capacity of the anaerobic filter could be raised even more rapidly than is shown in those Examples. Preferably the wet test meter is maintained at a substantially constant temperature, or the system is constructed to compensate for variations in the temperature of the wet test meter (as by sensing the wet test meter temperature, logging that value to the controller every 30 seconds and programming the computer to use that temperature signal and to multiply the volumetric rate signal by the appropriate temperature factor based on the perfect gas laws), or there is employed a wet test meter equipped with a suitable temperature compensator.

It will be understood that, in the operation of the control system the transmission and handling of data and control signals need not be effected entirely electrically. For instance compressed air or other analog (or digital) systems may be used for at least part of the control system.

Another aspect of the invention involves the use of the system described above to maintain an anaerobic filter at a substantially constant OL and at highest efficiency. In that case, once the desired OL has been attained (say an OL of 0.8 lb COD/cu ft/day, attained by operating at an efficiency of, say, about 80%), the controller is programmed so as to keep the OL at no more than 0.8 and to decrease the OL to a value below 0.8 only when the KL drops below some preset value. That pre-set value may be, for instance: (a) some fixed KL (e.g. 0.64, representing an efficiency of 80%) or (b) some percentage of the highest KL attained during that same particular period of constant OL (e.g. 90% of that highest KL). The end result of this control action is an increase in the efficiency of the system to a level which may be well above the set efficiency. Only when the KL falls below the pre-set value will the normal program resume control, lowering OL to follow the KL value. In some situations, such as when the proportion (in the feed) of inert compounds (such as pentaerythritol) increases and the OL is calculated on the basis of measurements of total COD of the feed, the efficiency may appear to drop (even though the anaerobic biomass is not being adversely affected) and the control scheme will then cause an unnecessary lowering of OL. To overcome this the control scheme may include means for measuring the rate of decrease of KL and may be programmed (e.g. using a general purpose computer) so that OL will not decrease below a pre-determined lower limit unless that measured rate of decrease of KL is relatively high and thus indicative of an adversely affected biomass.

As indicated earlier, the invention is useful in attaining a rapid rise in loading in a new filter. In Example 1 of the previously mentioned Witt et al application there is a description of a start-up procedure in which a start-up blend containing relatively non-toxic and non-inhibitory compounds (methanol, acetic acid and formic acid) is employed. Aqueous methanol alone or mixed with acetic acid may also be employed as the start-up feed. The start-up feed is preferably fed until the KL has reached at least about 0.1 lb COD/cu ft/day or more (e.g. 0.2) and the methane efficiency is above 50% (e.g. 60 or 70%). At that point the bacterial population may be large enough and varied enough to be increased rapidly by the use of the automatic control. During the initial period under such control several strategies may be used. In one strategy the controller is used, still with the start-up feed, to raise the capacity to a desired level (e.g. to an OL of 0.8) and then the start-up feed is gradually replaced by the effluent that is to be treated in the filter (e.g. the first day a blend of 95% start-up feed and 5% regular feed is used, the next day a 90-10 blend, etc. etc.). In another strategy the gradual replacement of the start-up feed by regular feed is begun at the close of the initial period mentioned above, i.e., at about the same time as the filter is placed under the control technique.

When the filter is operating well under anaerobic conditions the redox potential of the liquid in the filter (as measured on the liquid being recycled) is generally more negative than −400 mV, such as about −430 or −460 mV. Redox potential may be measured with a standard redox probe placed in series with the pH probe between valves V1 and V2.

FIGS. 7, 7A, 8 and 9 indicate that, at any given time, the filter appears to have a level of natural efficiency (which presumably depends on the types and amounts of bacteria in the filter in relation to the type and concentration of COD and of possibly toxic or inhibitory materials in the feed and recycle streams, at that time). Thus in FIG. 8 the level of KL during the period in which OL was kept constant was such as to indicate a natural efficiency of about 80%. The feeding of more COD (i.e. higher OL) than can be consumed at this natural efficiency appears to stimulate the growth of the methanogenic population and with it the production of more and more methane (see FIG. 8, for instance). When, however, the feed rate (OL) is set to give an efficiency higher than the natural efficiency the production of methane drops, as can be seen in FIG. 7; presumably the existing methanogenic population does not then have enough "food" to continue making methane at the previous rate. This reduction in feed rate (OL) does not, however, appear to harm the methanogenic population; see, for instance, the effect in FIGS. 7 and 7A in which the decrease in efficiency from 85% to 80% (the latter being slightly below the natural efficiency at the moment) caused the KL to rise rapidly, and see also FIG. 4 in which the effect of decreased feed rate prevailing at days 22 and 23 were overcome to a large extent within the following few days. Another strategy (not illustrated) which may be followed when it is desired to increase KL and OL rapidly while arriving at a relatively high efficiency is to program the controller to continually compute the natural efficiency and continually raise the predetermined set efficiency to almost that natural level (e.g. to a level which is a predetermined amount below the natural level such as 1% or 2% or 10% or 20% below the natural level).

Another aspect of this invention relates to the use of a second anaerobic filter directly receiving the outflow of the first, recycling, filter, preferably without intermediate substantial exposure to the atmosphere (or to otherwise aerobic conditions). This second filter may be operated with no recycle (or with very little recycle). It may be operated with no separate control of its feed rate (i.e. of the rate at which the outflow of the first filter is fed to it). It may be operated without a heater (or with very little heat input) since the liquid recycling in the first filter (and thus, also, the outflow of the first filter) has already been heated to approximately the optimum temperature for methanogenic activity of the biomass. It receives a feed of considerably lower strength (measured in g COD/l) than the feed to the first filter and effects a further significant decrease in strength, even when its size is considerably smaller (e.g. less than ½ the volume) of the first filter.

It has been found that, when the feed to the first filter contains relatively inert organic compounds (which pass substantially undegraded through the first filter) the second filter develops an increased ability to degrade those "inert" compounds. For example, in a test in which the feed to the first filter was a mixture of 16 g COD/l of degradable material (a mixture of 4 g COD/l of each of acetic acid, formaldehyde, methanol and butanol) and 4.9 g COD/l of relatively inert hydroxypropylated guar (guar gum chemically modified so that there is 0.53 hydroxypropyl ether group per monosaccharide unit of the guar), and the first filter was operated (without the methane-sensitive controls mentioned above) under such conditions that almost complete removal of the degradable material occurred in the first filter (which was 4 feet high and 12 inches in diameter), the addition of a much smaller second filter (4 feet high and 6 inches in diameter, i.e. ¼ the size of the first one) gave about double the degree of removal of the inert material; for instance, after a period of acclimation the degree of removal of the inert material in the first filter was around 25%, while the overall degree of removal of that inert material in the two filters was close to 50%. It may be that the second filter whose feed is relatively low in ordinarily degradable components and high in ordinarily inert components tends to develop a bacterial population that can degrade a greater proportion of those ordinary inert components. It will be understood that there may be a plurality of such smaller filters in series downstream of the first, recycling, filter.

When the first filter of the two-filter series is under automatic methane-sensitive control, the second filter is protected from toxic overloads since the presence of significant amounts of toxic material will result in a reduction in the feed rate (and concomitantly the outfall rate) to the first filter and a concomitant reduction in the loading on the second filter. That is, by volume, the rate of feed to the second filter is essentially the same as the outfall rate of the first filter, which is in turn essentially the same as the feed rate to the first filter.

The filters of the Examples were 4 feet high. In large commercial installations the filters will generally be much higher (e.g. they may be 20, 30 or 40 feet high), their diameters may be correspondingly larger, (e.g. diameters of 30 or 50 or 100 feet or more), and the average hydraulic velocities may be higher. As noted earlier in the Examples the hydraulic velocity (volumetric rate of total liquid divided by cross-sectional area of filter) was in the neighborhood of 1 to 2 cm per minute; for a filter some 30 feet high the feed rates may be such that the hydraulic velocities are some 5 to 10 times that velocity, e.g. about 5 to 20 cm per minute (about 10 to 40 ft/hr.). The detention time (volume of filter divided by volumetric rate of fresh feed) will usually be in the range of about 0.5 to 4 days (such as about 1 day).

In the Examples the controller determined the OL on the basis of the values of one-hour moving average of KL. In a large commercial filter the measured rate of gas production may be less subject to the effects of vibration and burping. Thus the instantaneous, or short-time average (e.g. 6 minute average), values of KL may therefore be employed as the controlling values, instead of using a one-hour moving average. This will make the controller even more responsive and facilitate rapid increases in OL (and KL) and rapid response to potentially upsetting conditions.

In the Examples the top of the filter was substantially under atmospheric pressure, while the bottom was under a head of about 4 feet or so of water. In a large commercial installation the lower part of the filter may be under considerable pressure (such as a pressure of about 30 feet of water) and the upper part may also be under some pressure (such as a back pressure of say 5 to 10 inches of water, owing to the manner of pumping the evolved gas). The higher pressures will cause more $CO_2$ to be dissolved in the liquid in the lower part of the filter which may cause a small drop in pH (such as a drop of about 0.2 pH unit).

In the Examples the liquid-gas separation zone was in a vessel located atop the filter. This zone may also be made part of the same vessel as the filter. For instance above the packing there may be a zone containing weirs over which the liquid (and suspended biomass) flows to a collection tank from which part is taken off as outfall and the remainder recycle; above the liquid level defined by the weirs there is a free space from which the gas is collected.

The invention has been illustrated primarily with petrochemical wastes having acidic pH's, below 6, such as in the range of about 3 to 5. It may also be used with neutral or alkaline streams (in which case the acid moiety is generated anaerobically within the filter by the action of the acid-forming bacteria). Such streams may contain sugars or higher carbohydrates or proteins (such as waste streams from food-processing industries). It has now been found that the recycling anaerobic filter will, after a relatively short acclimation period, even digest insoluble carbohydrates such as dispersed starch granules.

As discussed in the above-mentioned Witt et al application, the outfall of the process is preferably fed to an aerobic digester. The resulting aerobic sludge may then, in large part, by recycled to the controlled anaerobic filter. Conveniently, the aerobic sludge is recirculated at a constant predetermined rate and its COD value is measured at regular intervals so that the OL value supplied by the aerobic sludge is known and that value is fed to the controller, which is programmed to regulate the rate at which the fresh feed is pumped in so as to maintain the pre-set efficiency (or pre-set ΔL) based on the total OL (i.e., OL from sludge plus OL from fresh feed). Instead of feeding the aerobic sludge directly to the anaerobic filter, the sludge may be given a treatment (e.g. at high temperature under pressure, such as in the known Porteous process; see British patent 653,984 and Water Waste Treatment Journal I 543-5 [1960] to convert most of it to soluble material which is then fed to the controlled anaerobic filter.

The process described herein may be used to treat a wide variety of aqueous waste streams, such as those described in the above-mentioned Witt et al application. Unless otherwise indicated herein, the operating conditions, filter constructions, etc. disclosed in said Witt et al. application are suitable.

In a broader aspect of the invention, the control technique described herein may be used not only for anaerobic filters but also for other anaerobic methanogenic reactor vessels in which, like the anaerobic filters, a bed of the methanogenic bacteria is substantially retained in the anaerobic reactor vessel while the waste water passes upwards through that bed, the effluent from the vessel having a much lower bacterial concentration than is present in the bed of methanogenic bacteria. One such reactor is that described as the "Upflow Sludge Blanket (USB) Reactor" in the article by G. Lettinga et al entitled "Use of the Upflow Sludge Blanket (USB) Reactor Concept for Biological Waste water Treatment, especially for Anaerobic Treatment" in Biotechnology and Bioengineering Vol. XII No. 4 April 1980 pages 699-734; this reactor and its operation are also described in the article by G. Lettinga entitled "Direct Anaerobic Treatment Handles Wastes Effectively" in the journal Industrial Wastes for January/February, 1979 pages 18-24, 40 and 41, German Offenlegungschrifte 29 20978 and 2921070 both published 29.11.79, the article by Lettinga et al entitled "Anaerobic Treatment of Methanolic Wastes" in the journal "Water Research" Vol. 13 (1979) pages 725 to 737 and the article entitled "Feasibility of Anaerobic Digestion for the Purification of Industrial Waste Waters" by Lettinga in Documentation—Europe Sewage & Refuse Symposium EAS, 4th, Munich 1978 (pub. by Abwassertechnische Vereinigung St. Augustin, German Federal Republic 5205) pages 226-256, the paper on "Elimination of Organic Wastes from Surface Water" given by Th. M. Van Bellegem at the 13th International TNO Conference at Rotterdam 27-28 March 1980 (paper available from Netherlands Organization for Applied Scientific Research TNO) and the article entitled "A Pilot Scale Anaerobic Upflow Reactor Treating Distillery Wastewaters" by Pipyn et al in Biotechnology Letters 1, pages 495-500 (1979). Another such reactor is that in which the bacteria are attached to support particles, such as described in the article by M. S. Switzenbaum et al entitled "Anaerobic Attached-Film Expanded-Bed Reactor Treatment" in Journal WPCF Vol. 52 No. 7 (July 1980) pages 1953-1965, the articles by B. Atkinson et al entitled "Process Intensification Using Cell Support Systems" (in Process Biochemistry, May 1980 pages 24-32) and "Biological Particles of Given Size, Shape and Density for Use in Biological Reactors" (in Biotechnology and Bioengineering Vol. XXI pages 193-200 (1979) and in published U.K. patent application GB 2005 181 A published 2 May, 1979. In both these types of reactors the bacteria are present on relatively large particles or flowable aggregates of such size and density that they have a high sedimentation velocity in still water such that even at high loading conditions (such as hydraulic retention times of less than 2 days, e.g., 1 day or less) the concentration of bacterial suspended solids in the effluent at the top of the reactor is relatively low, such as less than 0.05 gram (e.g. 0.01 gram) of bacterial suspended solids per gram of COD in the feed to the reactor, and the bacteria are retained in the reactor for long periods of time (their average residence time in the reactor being, for instance, over 10 days such as about 30 or 100 days or more).

It is also within the broader scope of the invention to employ the same control technique (described above) in the operation of anaerobic filters (or other anaerobic reactors described above) in which the bacteria are of the well known sulfate-reducing type rather than the methanogenic type. In this modification the control parameter is the rate of production of hydrogen sulfide gas rather than the rate of production of methane. A wastewater having a high sulfate concentration is used. For example, an aqueous waste rich in sulfuric acid or sulfates may be mixed with an aqueous organic waste, such as described earlier herein, and the resulting mixture (containing several percent, such as 5% or more, of sulfate ion) may be fed to an anaerobic filter containing a biomass of anaerobic sulfate-reducing bacteria, by means of which the sulfate ion is converted to $H_2S$ and the organic compounds to $CO_2$ (the oxygen being supplied by the reduction of the sulfate ion); the $H_2S$ gas may then be converted catalytically, in known manner, to elemental sulfur.

As previously noted, the calculation of KL for a methanogenic reactor may be based on the COD value of methane, which is 64 grams of COD per gram mole (i.e., 4 lbs. COD per lb of methane). The COD value of hydrogen sulfide is also 64 grams per gram mole. Thus the KL (in metric units of kg COD per $m^3$ per day) for an anaerobic filter producing hydrogen sulfide is the volumetric rate of flow (at standard conditions and expressed as $m^3$ per day) of the offgas multiplied by the mol fraction of hydrogen sulfide in the offgas multiplied by 0.064 kg COD and divided by the product of the volume (in $m^3$) of the anaerobic filter and the molar volume (in $m^3$); this KL metric value can of course be converted routinely to KL units of pounds COD per $ft^3$ per day by multiplying by 0.0625.

Under certain conditions, such as relatively low sulfate concentrations, the $H_2S$-producing reactor may also produce significant proportions of methane in the offgas. In that case the control may be based on a KL value which is determined on the basis of both $H_2S$ and methane, e.g. by using the total mol fraction of $H_2S$ and $CH_4$ combined, instead of simply the mol fraction of $H_2S$, in the calculation described above.

In the operation of the $H_2S$-producing anaerobic filter, or similar reactor, it may be desirable to recirculate part of the offgas (i.e. after removal of $H_2S$) to the bottom of the reactor to flow upward therethrough to help scrub $H_2S$ therefrom, as by the action of the $CO_2$ in the offgas that is recycled. For instance, the stream of offgas from the anaerobic filter may be treated (e.g. with ferric ion by the known "Cataban" process or with $SO_2$ by the known Claus process) to convert the $H_2S$ to sulfur and the remaining gas (after removal of sulfur) may be recycled to the anaerobic filter.

The embodiments of the invention in which an exclusive property or privilege is claimed are defined as follows:

1. Process for the treatment of an organic wastewater stream containing COD in a recycling anaerobic filter which contains methanogenic bacteria, operates at a COD feed rate, OL, which is at least 0.5 lb COD/cu. ft./day, and produces a stream of gas comprising methane, wherein the improvement comprises continually carrying out an alternating sequence of steps at least once per four hour period, the steps of said sequence comprising,
(a) a step of measuring the rate of production of methane in said gas stream and thereby determining the rate, KL, at which COD is removed from said filter as methane, and
(b) a step of setting the COD feed rate, OL, to said filter to maintain a predetermined ratio between the KL determined in said step a and the OL set in said step b,
said predetermined ratio of KL to OL, both KL and OL being expressed in the same units of lbs. COD/cu. ft./day, having a value of about 0.65 to 0.9.

2. Process as in claim 1 and including the step of feeding the outfall of said recycling anaerobic filter directly to a second anaerobic filter.

3. Process as in claim 2 in which said waste stream is heated in said recycling anaerobic filter and said outfall is fed, in thus-heated condition, directly to said second filter.

4. Process as in claim 1 in which said sequence of steps is carried out at least once per hour.

5. Process as in claim 4 in which said alternating sequence is effected so frequently that the magnitudes of OL changes are each less than 10%.

6. Process as in claim 1 in which said sequence of steps is carried out at least once per 15-minute period.

7. Process as in claim 1 in which the KL is increased, by carrying out said alternating sequence continually, to a value of at least 1.5 lb. COD/cu. ft./day.

8. Process as in claim 1 in which, by carrying out said alternating sequence continually, the amount of biomass in said filter is raised to such a level that the amount of free liquid in said filter is less than 70% of the void volume of the filter 9. Process as in claim 8 in which said amount of free liquid is less than 50% of said void volume.

* * * * *

UNITED STATES PATENT AND TRADEMARK OFFICE
CERTIFICATE OF CORRECTION

PATENT NO. : 4,352,738
DATED : October 5, 1982
INVENTOR(S) : George A. Blay, Enrique R. Witt It is certified that error appears in the above–identified patent and that said Letters Patent are hereby corrected as shown below:

In column 10, last line thereof, for "5 COD/1" read-- 5 g COD/1 --.

Signed and Sealed this

Twelfth Day of April 1983

[SEAL]

Attest:

Attesting Officer

GERALD J. MOSSINGHOFF

Commissioner of Patents and Trademarks